(12) United States Patent
Nawaz et al.

(10) Patent No.: US 10,737,236 B2
(45) Date of Patent: Aug. 11, 2020

(54) STRUCTURAL CATALYST WITH INTERNAL HEAT TRANSFER SYSTEM FOR EXOTHERMIC AND ENDOTHERMIC REACTIONS

(71) Applicant: SABIC Global Technologies B.V., Bergen op Zoom (NL)

(72) Inventors: Zeeshan Nawaz, Riyadh (SA); Khalid Karim, Riyadh (SA)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 15/777,732

(22) PCT Filed: Nov. 18, 2016

(86) PCT No.: PCT/IB2016/056959
§ 371 (c)(1),
(2) Date: May 21, 2018

(87) PCT Pub. No.: WO2017/089935
PCT Pub. Date: Jun. 1, 2017

(65) Prior Publication Data
US 2018/0333695 A1 Nov. 22, 2018

Related U.S. Application Data

(60) Provisional application No. 62/258,784, filed on Nov. 23, 2015.

(51) Int. Cl.
*B01J 8/02* (2006.01)
*B01J 19/24* (2006.01)
(Continued)

(52) U.S. Cl.
CPC ......... *B01J 19/2485* (2013.01); *B01J 8/0285* (2013.01); *B01J 19/0013* (2013.01);
(Continued)

(58) Field of Classification Search
None
See application file for complete search history.

(56) References Cited

U.S. PATENT DOCUMENTS 1,604,739 A * 10/1926 Downs .................. B01J 8/06
422/614
3,147,084 A 9/1964 Franzen et al.
(Continued)

FOREIGN PATENT DOCUMENTS

CN 201580062755 5/2017
DE 2942359 A1 6/1980
(Continued)

OTHER PUBLICATIONS

Machine translation for DE 198 39 782 A1. Retrieved from Espacenet website on Nov. 19, 2019. (Year: 2019).*
(Continued)

*Primary Examiner* — Jennifer A Leung
(74) *Attorney, Agent, or Firm* — Norton Rose Fulbright US LLP (57) ABSTRACT

A reactor for efficient control of endothermic and exothermic catalytic reactions, including, for example, Fischer Tropsch reactions. Also disclosed are methods of delivering coolant materials and gasification source materials to the reactor.

20 Claims, 5 Drawing Sheets

(51) Int. Cl.
*B01J 19/32* (2006.01)
*C10G 2/00* (2006.01)
*B01J 19/00* (2006.01)
*C07C 29/152* (2006.01)

(52) U.S. Cl.
CPC .......... *B01J 19/249* (2013.01); *C07C 29/152* (2013.01); *C10G 2/34* (2013.01); *B01J 2219/00076* (2013.01); *B01J 2219/2411* (2013.01); *B01J 2219/2428* (2013.01); *B01J 2219/2462* (2013.01); *B01J 2219/2479* (2013.01); *C10G 2400/22* (2013.01)

(56) References Cited

U.S. PATENT DOCUMENTS

| | | | | |
|---|---|---|---|---|
| 3,357,916 | A | * | 12/1967 | Smith .................. B01J 19/243 208/120.05 |
| 4,101,287 | A | * | 7/1978 | Sweed .................. B01J 8/067 165/165 |
| 4,533,584 | A | * | 8/1985 | Takeuchi ............... B01J 15/00 422/180 |
| 4,971,770 | A | | 11/1990 | Alagy et al. |
| 5,869,541 | A | | 2/1999 | Euzen |
| 6,056,932 | A | | 5/2000 | Von Hippel et al. |
| 6,747,162 | B2 | | 6/2004 | Olbert |
| 7,012,103 | B2 | | 3/2006 | Espinoza |
| 7,833,498 | B2 | * | 11/2010 | Goebbel ................ B01J 8/067 422/198 |
| 8,524,787 | B2 | | 9/2013 | Ermolaev |
| 2002/0048541 | A1 | | 4/2002 | Schodel et al. |
| 2002/0125001 | A1 | * | 9/2002 | Kelly .................. F28F 7/02 165/165 |
| 2007/0009426 | A1 | | 1/2007 | Leveson |
| 2008/0233043 | A1 | | 9/2008 | Olbert |
| 2012/0308442 | A1 | | 12/2012 | Duwig |
| 2013/0020054 | A1 | | 1/2013 | Tomlinson |
| 2013/0217793 | A1 | | 8/2013 | Wang et al. |
| 2013/0274508 | A1 | | 10/2013 | DeCourcy |
| 2014/0343175 | A1 | * | 11/2014 | Saxton, Jr. ............. C07C 1/0435 518/715 |
| 2017/0306243 | A1 | | 10/2017 | Nawaz et al. |

FOREIGN PATENT DOCUMENTS

| | | | |
|---|---|---|---|
| DE | 2903582 A1 | 8/1980 | |
| DE | 19839782 A1 * | 3/2000 | .............. B01J 23/31 |
| EP | 0025308 A1 | 3/1981 | |
| EP | 0208929 A1 | 1/1987 | |
| EP | 0848990 A2 | 6/1998 | |
| EP | 2547434 A1 | 1/2013 | |
| EP | 15800978.7 | 6/2017 | |
| GB | 303192 A * | 12/1928 | ................ B01J 8/06 |
| GB | 845366 A * | 8/1960 | ................ B01J 8/06 |
| GC | 30422 | 11/2015 | |
| GC | 32414 | 11/2016 | |
| IN | 201717016590 | 5/2017 | |
| JP | H09-217905 A | 8/1997 | |
| JP | 2017-527214 | 5/2017 | |
| RU | 2017121279 | 6/1917 | |
| WO | WO-2004/033084 A1 | 4/2004 | |
| WO | WO-2009/118080 A1 | 10/2009 | |
| WO | WO-2011/116157 A1 | 9/2011 | |
| WO | WO-2013/093422 A1 | 6/2013 | |
| WO | WO-2013/126341 A1 | 8/2013 | |
| WO | PCT/IB2015/058596 | 11/2015 | |
| WO | WO-2016/079630 A2 | 5/2016 | |
| WO | PCT/IB2016/056959 | 11/2016 | |

OTHER PUBLICATIONS

Anxionnaz, Z., et al., Heat exchange/reactors (hex reactors): concepts, technologies: state-of-the-art. Chem Eng Process: Process Intensification. 2008; 47(12):2029-50.

DeVries, W., Advanced shell-and-tube heat exchangers. Code 1.1.2, European Roadmap for Process Intensification, Appendix 1, pp. 9-10 (2007) (87 pages).

DeVries, W., European Roadmap for Process Intensification. www.creative-energy.org (2007) (53 pages).

Jiamrittiwong, P. et al., Investigations of hydrodynamics and heat transfers in a modified reactor using fluid mixers. Adv Mater Res. 2013; 805-6:1250-6.

Narataruksa, P. et al., Conversion enhancement of tubular fixed-bed reactor for Fischer-Tropsch synthesis using static mixer. J Nat Gas Chem. 2012; 21(4):435-44.

Sulzer Chemtech, Mixing and reaction technology, pace-setting technology, worldwide. Sulzer Chemtech. pp. 1-20.

International Search Report and Written Opinion dated Jun. 8, 2016 by the International Searching Authority for Patent Application No. PCT/IB2015/058596, which was filed on Nov. 6, 2015 and published as WO 2016/079630 dated May 26, 2016 (Applicant—Sabic Global Technologies B.V.) (18 pages).

International Preliminary Report on Patentability dated May 23, 2017 by the International Searching Authority for Patent Application No. PCT/IB2015/058596, which was filed on Nov. 6, 2015 and published as WO 2016/079630 dated May 26, 2016 (Applicant—SABIC Global Technologies B.V.) (11 pages).

Preliminary Amendment filed on May 12, 2017 with the U.S. Patent and Trademark Office for U.S. Appl. No. 15/526,364, filed May 12, 2017 and published as U.S. Pat. No. 2017/0306243 dated Oct. 26, 2017 (Inventor—Nawaz et al.; Applicant—SABIC Global Technologies B.v.) (11 pages).

Restriction Requirement dated Apr. 10, 2018 by with the U.S. Patent and Trademark Office for U.S. Appl. No. 15/526,364, filed May 12, 2017 and published as U.S. Pat. No. 2017/0306243 dated Oct. 26, 2017 (Inventor—Nawaz et al.; Applicant—SABIC Global Technologies B.v.) (8 pages).

International Search Report and Written Opinion dated Feb. 24, 2017 by the International Searching Authority for Patent Application No. PCT/IB2016/056959, which was filed on Nov. 18, 2016 and published as WO 2017/089935 dated Jun. 1, 2017 (Inventor—Nawaz et al.; Applicant—SABIC Global Technologies B.V.) (9 pages).

U.S. Appl. No. 62/082,170, filed Nov. 20, 2014, Nawaz et al. (SABIC Global Technol., B.V.).

U.S. Appl. No. 15/526,364 (U.S. Pat. No. 2017/0306243), filed May 12, 2017 (dated Oct. 26, 2017), Nawaz et al. (SABIC Global Technol., B.V.).

U.S. Appl. No. 62/258,784, filed Nov. 23, 2015, Nawaz et al. (SABIC Global Technol., B.V.).

\* cited by examiner

STRUCTURAL CATALYST WITH INTERNAL HEAT TRANSFER SYSTEM FOR EXOTHERMIC AND ENDOTHERMIC REACTIONS

CROSS-REFERENCE TO RELATED APPLICATIONS

This application is a U.S. National Phase Application of International Application No. PCT/IB2016/056959, filed Nov. 18, 2016, which claims priority to and the benefit of the filing date of U.S. Provisional Application No. 62/258,784, filed Nov. 23, 2015, which applications are hereby incorporated herein by reference in their entirety.

BACKGROUND

Among the various chemical reactions occurring in industrial reactors, the use of catalytic gas-solid reactions is widespread. A packed bed reactor is commonly used for these types of reactions. Conventional packed bed reactors are associated with various difficulties and disadvantages, including pressure drop, intra particle diffusion limitations, flow channeling, and heat transfer limitations.

Structured catalyst reactors are frequently used to address these challenges. These structured catalyst reactors are commonly utilized when there is a need for controlled endothermic or exothermic reactions. However, existing structured catalyst reactors, while demonstrating higher performance in comparison to the packed bed reactors, still have a number of drawbacks, including high cost, weight, thermal resistance, and heat management, among others.

Structured catalyst reactors are commonly used in the Fischer-Tropsch catalytic process. The Fisher-Tropsch process involves the conversion of carbon monoxide and hydrogen gas, known as syngas, to a mixture of liquid and gaseous hydrocarbons (carrying a number of —$CH_2$— moieties). The feed (syngas) for the Fisher-Tropsch process can originate from any gasification source, for example, a natural gas, biomass, or coal. Important products of the Fisher-Tropsch reaction include gaseous hydrocarbons, such as lower olefins, paraffins, or alcohols, and liquid hydrocarbons, such as higher olefins, paraffins and alcohols. The Fisher-Tropsch reaction is highly exothermic (releasing about 145 KJ per each "$CH_2$" moiety formed) and therefore effective heat transfer and temperature controls are important prerequisites for the successful operation. Furthermore, the reaction operability range, with pressures between 1-30 bar and temperatures ranging from 200° C. to 350° C., requires an additional control to prevent formation of local hot spots responsible for the deterioration of the catalyst. Thus, there is a need for continuous heat removal during the reaction to prevent metallic catalyst deactivation and formation of undesirable products.

Accordingly, there remains a need for a reactor that provides an efficient control over endothermic and exothermic chemical reactions, such as those carried out in the presence of a catalyst. For example, there is a need for a reactor for the Fischer-Tropsch catalytic processing of the syngas that ensures continuous heat removal during the catalytic reaction. Still further, there is a need for a method of efficiently performing the Fischer-Tropsch catalytic process, by continuous removal of the resultant heat.

Accordingly, a reactor and method useful for the efficient catalytic processing and control over endothermic and exothermic chemical reactions are described herein.

SUMMARY

Disclosed herein is a reactor having a longitudinal axis, the reactor comprising: a housing having an outer wall, the outer wall defining at least one gas inlet and at least one coolant inlet; a frame positioned within the housing, the frame comprising a plurality of interior surfaces and a plurality of exterior surfaces, wherein the plurality of interior surfaces cooperate to define a plurality of interconnected coolant channels within the frame, wherein the plurality of exterior surfaces define a plurality of isolated conduits, each conduit of the plurality of isolated conduits having a respective longitudinal axis that is substantially parallel to the longitudinal axis of the reactor, wherein at least a portion of the at least one exterior surface that defines each respective conduit is coated with at least one catalyst material to position the at least one catalyst material within the conduit, wherein the plurality of interconnected coolant channels are positioned in fluid communication with the at least one coolant inlet, and wherein the plurality of conduits are positioned in fluid communication with the at least one gas inlet.

Also disclosed herein is a reactor having a longitudinal axis, the reactor comprising: a housing having an outer wall, the outer wall defining at least one gas inlet and at least one coolant inlet; and a plurality of elongate catalyst support elements, each catalyst support element having an inner surface and an outer surface, the inner surface of each catalyst support element defining a coolant channel within the catalyst support element, wherein at least a portion of the outer surface of each catalyst support element is coated with at least one catalyst material, wherein the coolant channels of the plurality of catalyst support elements are positioned in fluid communication with the at least one coolant inlet, wherein the outer surfaces of the plurality of catalyst support elements are positioned in fluid communication with the at least one gas inlet, and wherein the coolant channels of the plurality of elongate catalyst support elements are fluidly isolated from the at least one gas inlet.

Further disclosed herein is a reactor having a longitudinal axis, the reactor comprising: a housing having an outer wall, the outer wall defining at least one gas inlet and at least one coolant inlet; and at least one heat transfer assembly positioned within the housing, at least one heat transfer assembly positioned within the housing, each heat transfer assembly of the at least one heat transfer assembly comprising at least one coolant conduit and a plurality of flange elements, each coolant conduit of the at least one coolant conduit having an outer surface and a longitudinal axis that is substantially parallel to the longitudinal axis of the reactor, each flange element of the plurality of flange elements is oriented substantially perpendicularly relatively to the longitudinal axis of the reactor, wherein at least a portion of each flange element of the at least one heat transfer assembly is coated with at least one catalyst material, wherein at least a portion of each flange element of the at least one heat transfer assembly is coated with at least one catalyst material, wherein the at least one coolant conduit of the at least one heat transfer assembly is positioned in fluid communication with the at least one coolant inlet, wherein each flange element of the at least one heat transfer assembly is positioned in fluid communication with the at least one gas inlet, and wherein the at least one coolant conduit of the at least one heat transfer assembly is fluidly isolated from the at least one gas inlet.

Further disclosed herein is a method of using the inventive reactors comprising: delivering at least one coolant material to the at least one coolant inlet of the reactor; and delivering at least one gasification source material to the at least one gas inlet of the reactor.

Additional advantages will be set forth in part in the description which follows, and in part will be obvious from the description, or can be learned by practice of the aspects described below. The advantages described below will be realized and attained by means of the devices, systems, methods, and combinations thereof particularly pointed out in the appended claims. It is to be understood that both the foregoing general description and the following detailed description are exemplary and explanatory only and are not restrictive of the invention, as claimed.

DESCRIPTION OF THE FIGURES

The accompanying figures, which are incorporated in and constitute a part of this specification, illustrate several aspects, and together with the description, serve to explain the principles of the invention.

DETAILED DESCRIPTION

The present invention can be understood more readily by reference to the following detailed description of the invention.

Disclosed herein are materials, compounds, compositions, and components that can be used for, can be used in conjunction with, can be used in preparation for, or are products of the disclosed method and compositions. It is to be understood that when combinations, subsets, interactions, groups, etc. of these materials are disclosed that while specific reference of each various individual and collective combinations and permutation of these compounds cannot be explicitly disclosed, each is specifically contemplated and described herein. This concept applies to all aspects of this disclosure including, but not limited to, steps in methods of making and using the disclosed compositions. Thus, if there are a variety of additional steps that can be performed it is understood that each of these additional steps can be performed with any specific aspect or combination of aspects of the disclosed methods, and that each such combination is specifically contemplated and should be considered disclosed.

All publications mentioned herein are incorporated herein by reference to disclose and describe the methods and/or materials in connection with which the publications are cited.

1. Definitions

In this specification and in the claims which follow, reference will be made to a number of terms which shall be defined to have the following meanings:

As used in the specification and in the claims, the term "comprising" can include the aspects "consisting of" and "consisting essentially of." Unless defined otherwise, all technical and scientific terms used herein have the same meaning as commonly understood by one of ordinary skill in the art to which this invention belongs. In this specification and in the claims which follow, reference will be made to a number of terms which shall be defined herein.

As used in the specification and the appended claims, the singular forms "a," "an" and "the" include plural referents unless the context clearly dictates otherwise. Thus, for example, reference to "a hydrocarbon" includes mixtures of two or more hydrocarbons.

As used herein, the terms "about" and "at or about" mean that the amount or value in question can be the value designated some other value approximately or about the same. It is generally understood, as used herein, that it is the nominal value indicated ±10% variation unless otherwise indicated or inferred. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The terms "first," "first plurality of coolant channels," "second," "second plurality of coolant channels," and the like, where used herein, do not denote any order, quantity, or importance, and are used to distinguish one element from another, unless specifically stated otherwise.

As used herein, the terms "optional" or "optionally" means that the subsequently described event or circumstance can or cannot occur, and that the description includes instances where said event or circumstance occurs and instances where it does not.

As used herein, the terms "syngas" or "synthesis gas" are used interchangeably herein.

As used herein, the terms "lower olefin," "lower paraffin," or "lower alcohol" are used to describe lower molecular weight C2-C6 olefins, paraffins and alcohols.

As used herein, the terms "higher olefin," "higher paraffin," or "higher alcohol" are used to describe lower molecular weight C7-C20 olefins, paraffins and alcohols.

Optionally, as used herein, the term "substantially parallel" can refer to an axis or surface that is within about 10 to about 15 degrees of being parallel to a reference axis or surface.

Optionally, as used herein, the term "substantially perpendicular" can refer to an axis or surface that is within about 10 to about 15 degrees of being perpendicular to a reference axis or surface.

Moreover, it is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of aspects described in the specification.

2. Reactor

In some aspects, described herein is an exemplary reactor configuration wherein at least a portion of the reactor is coated with at least one catalyst material.

a. Reactor Having a Frame with Interconnected Coolant Channels

Figure 1:
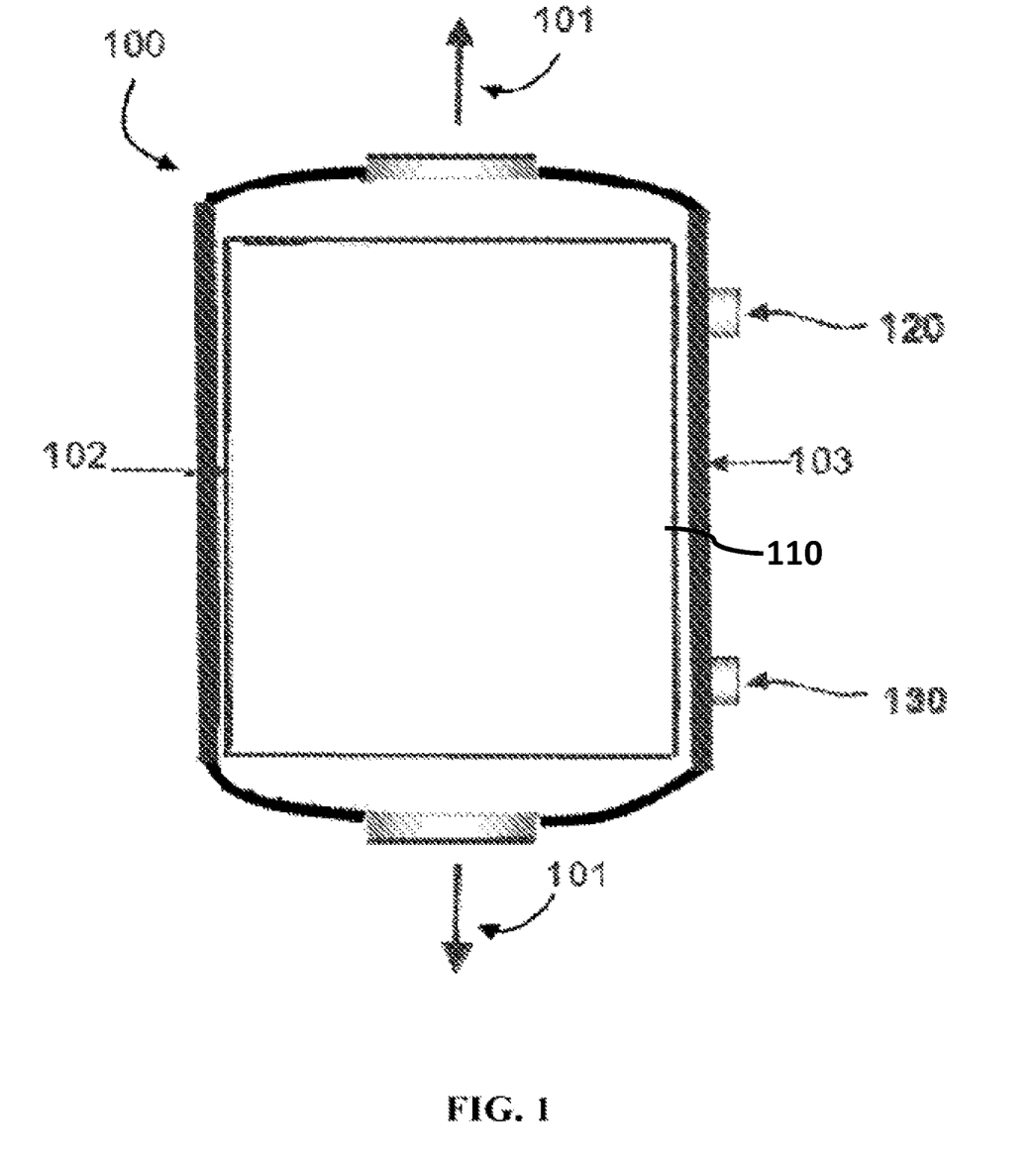
FIG. 1 is an exterior side perspective view of an exemplary reactor as disclosed herein.
Figure 2:
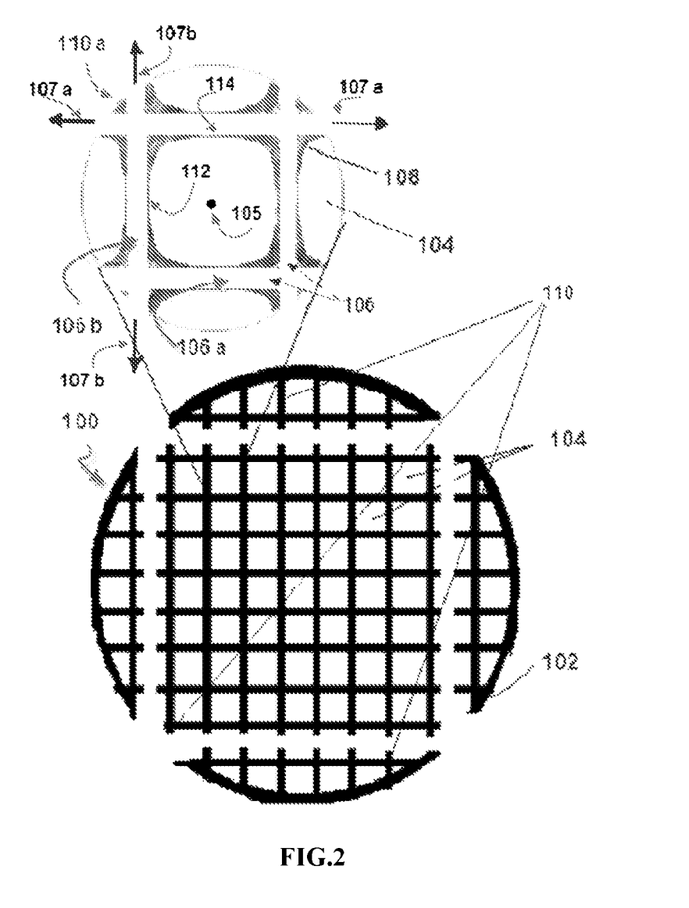
FIG. 2 is a cross-sectional end view of an exemplary reactor as disclosed herein.
Figure 3:
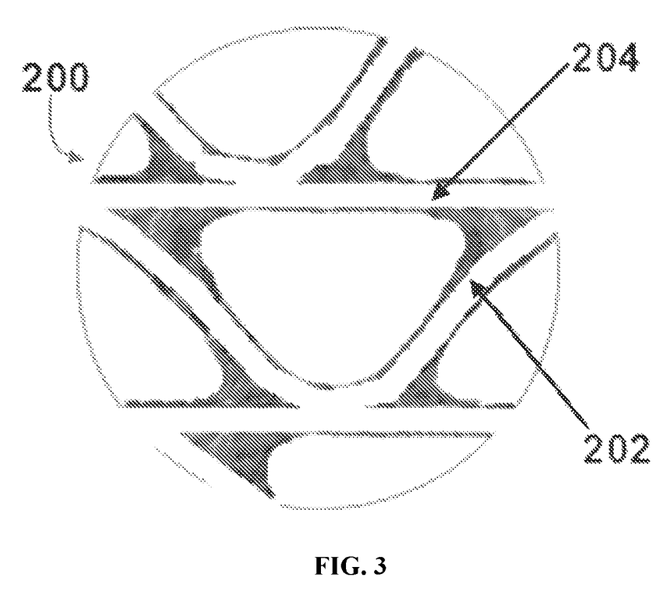
FIG. 3 is a close-up cross-sectional end view of the frame and coolant channels of another exemplary reactor as disclosed herein.

In some aspects, and with reference to FIGS. 1-3, disclosed herein is a reactor having a longitudinal axis, the reactor comprising: a housing and a frame positioned within the housing. In some aspects, the housing can have an outer wall, wherein the outer wall defines at least one gas inlet and at least one coolant inlet. In other aspects, the frame can comprise a plurality of interior surfaces and a plurality of exterior surfaces. In some aspects, the plurality of interior surfaces can cooperate to define a plurality of interconnected coolant channels within the frame. In other aspects, the plurality of exterior surfaces can define a plurality of isolated conduits, wherein each conduit of the plurality of isolated conduits has a respective longitudinal axis that is substantially parallel to the longitudinal axis of the reactor. In yet other aspects, at least a portion of the at least one exterior surface that defines each respective conduit can be coated with at least one catalyst material to position the at least one catalyst material within the conduit. In still further aspects, the plurality of interconnected coolant channels can be positioned in fluid communication with the at least one coolant inlet. In yet further aspects, the plurality of conduits can be positioned in fluid communication with the at least one gas inlet.

FIG. 2 shows a non-limiting exemplary aspect of a reactor as disclosed herein. FIG. 2 shows a reactor 100 having a longitudinal axis 101 and comprising a housing 102 and a frame 110. The housing 102 has an outer wall 103 that defines at least one gas inlet 120 and at least one coolant inlet 130. The frame 110 has a plurality of exterior surfaces 112 and a plurality of interior surfaces 114. The plurality of exterior surfaces 112 define a plurality of isolated conduits 104, and the plurality of interior surfaces 114 define a plurality of interconnected coolant channels 106. Each conduit 104 has a respective longitudinal axis 105. A close-up sectional view of the frame 110a shows a plurality of interconnected coolant channels 106 and a catalyst 108 deposited within a conduit 104.

In some optional aspects, a first plurality of coolant channels 106a have longitudinal axes 107a that extend perpendicularly or substantially perpendicularly to the longitudinal axes 105 of the plurality of conduits 104, and wherein each coolant channel of a second plurality of coolant channels 106b has a variable profile that extends and is angled relative to the longitudinal axes of the first plurality of coolant channels. In other aspects, the variable profile of each coolant channel of the second plurality of coolant channels can optionally correspond to a serpentine pattern or substantially serpentine pattern extending between and in fluid communication with adjacent coolant channels of the first plurality of coolant channels. FIG. 3 shows an exemplary frame 200 of a reactor 100 in which a second plurality of coolant channels 202 is positioned between and oriented perpendicularly or substantially perpendicularly relative to a first plurality of coolant channels 204.

In some aspects the plurality of interconnected coolant channels can comprise one or more coolant materials. In some aspects the plurality of interconnected coolant channels can be in a fluid communication with at least one coolant inlet. In some aspects, the coolant material is delivered to the plurality of interconnected coolant channels through the at least one coolant inlet.

As further disclosed herein, in some aspects, the plurality of interconnected coolant channels of the frame can comprise a first plurality of coolant channels and a second plurality of coolant channels, wherein the second plurality of coolant channels are oriented perpendicularly or substantially perpendicularly to the first plurality of coolant channels to thereby create a grid of coolant channels. In some aspects, the plurality of interconnected coolant channels of the frame can comprise from about 10 to about 50,000 coolant channels, including exemplary values of about 25, about 50, about 75, about 100, about 250, about 500, about 1,000, about 2,500, about 5,000, about 7,500, about 10,000, about 20,000, about 30,000, and about 40,000 coolant channels. Still further, the plurality of interconnected coolant channels can comprise a number of channels in any range derived from any two of the above stated values. For example, the plurality of interconnected coolant channels can comprise from about 10 to about 40,000 of coolant channels, or from about 100 to about 20,000 coolant channels, or from about 1,000 to about 10,000 coolant channels.

In some aspects, each of the plurality of interconnected coolant channels can have dimensions from about 0.1 µm to about 10 mm in a diameter.

It is further understood that each of the plurality of interior surfaces and each of the plurality of exterior surfaces can be defined by a respective wall of each of the plurality of interconnected coolant channels. In certain aspects, a wall thickness can be determined by one of ordinary skill in the art to ensure an efficient heat transfer between interconnected coolant channels and to withstand pressure drops within the interconnected coolant channels.

In some aspects, where the frame comprises first and second pluralities of coolant channels as disclosed herein, the flow of coolant material in the first plurality of coolant channels is parallel or substantially parallel to the flow of coolant material in the second plurality of coolant channels. In yet other aspects, the flow of coolant material in the first plurality of coolant channels is in counter-flow (optionally, perpendicular or substantially perpendicular) to the flow of coolant material in the second plurality of coolant channels. It is further understood that the flow rate of the coolant material in the plurality of coolant channels can be adjustable depending on the specific application. It is further understood that the maximum and minimum flow rate of the coolant material in the plurality of coolant channels can depend on the dimensions of the plurality of coolant channels and can be easily defined by one of ordinary skill in the art depending on the specific application.

b. Reactor Having a Plurality of Elongate Catalyst Support Elements

Figure 4:
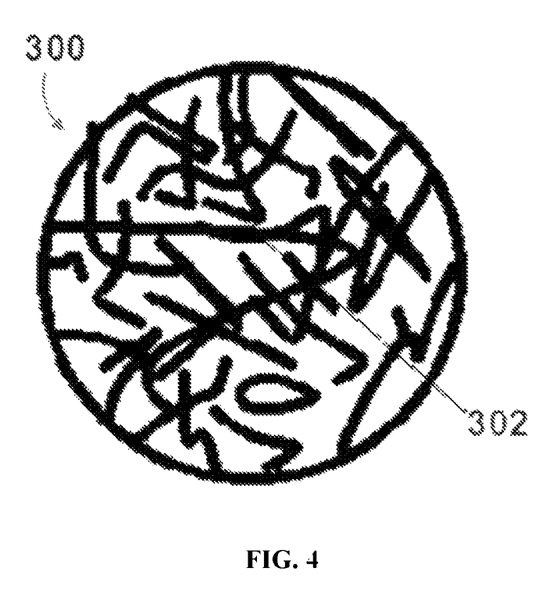
FIG. 4 is a cross-sectional end view of another exemplary reactor as disclosed herein.

In certain aspects, and with reference to FIG. 4, the reactor can have a longitudinal axis and comprise a housing and a plurality of elongate catalyst support elements. In certain aspects, the housing can have an outer wall, wherein the outer wall defines at least one gas inlet and at least one coolant inlet. In other aspects, each catalyst support element of the plurality of elongate catalyst support elements can have an inner surface and an outer surface, wherein the inner surface of each catalyst support element defines a coolant channel within the catalyst support element. In some other aspects, at least a portion of the outer surface of each catalyst support element can be coated with at least one catalyst material. In yet other aspects, the coolant channels of the plurality of catalyst support elements can be positioned in fluid communication with the at least one coolant inlet. In further aspects, the outer surfaces of the plurality of catalyst support elements can be positioned in fluid communication with the at least one gas inlet. In still further aspects, the coolant channels of the plurality of elongate catalyst support elements can be fluidly isolated from the at least one gas inlet.

In certain aspects, the at least one elongate catalyst support element can comprise a rigid material, a flexible material, or a combination thereof. In yet other aspects, the at least one elongate catalyst support element can comprise a rigid material. In still further aspects, the at least one elongate catalyst support element can comprise a flexible material. In yet other aspects, the at least one elongate catalyst support element can comprise a sponge material.

In some aspects, the plurality of elongate catalyst support elements disclosed herein can be uniformly dispersed within the housing. In other aspects, the plurality of elongate catalyst support elements can be randomly dispersed within the housing. In yet other aspects, the plurality of elongate support elements can be dispersed within the hosing in a specifically defined configuration. In other aspects, the specifically defined configuration can be any configuration required to achieve a desirable reaction conditions. It is further understood that the specifically defined configuration can be easily determined by one of ordinary skill in the art depending on the desired reaction outcomes.

In some aspects, the plurality of elongate catalyst support elements can comprise from about 10 to about 50,000 catalyst support elements, including exemplary values of about 25, about 50, about 75, about 100, about 250, about 500, about 1,000, about 2,500, about 5,000, about 7,500, about 10,000, about 20,000, about 30,000, and about 40,000 catalyst support elements. Still further, the plurality of elongate catalyst support elements can comprise a number of elements in any range derived from any two of the above stated values. For example, the plurality of elongate catalyst support elements can comprise from about 10 to about 40,000 of catalyst support elements, or from about 100 to about 20,000 catalyst support elements, or from about 1,000 to about 10,000 catalyst support elements.

In some aspects, the coolant channels defined within the catalyst support element can have dimensions from 0.1 μm to about 10 mm in a diameter.

It is further understood that the inner and the outer surfaces of the plurality of elongate catalyst support elements can be defined by a respective wall of each of the coolant channels within the catalyst support element. In certain aspects, a wall thickness can be determined by one of ordinary skill in the art to ensure an efficient heat transfer to the interconnected coolant channels and to withstand pressure drops within the coolant channels.

In yet other aspects, the coolant channels defined within the catalyst support element can be configured to receive one or more coolant materials. In some aspects, the coolant channels defined within the catalyst support element are in a fluid communication with at least one coolant inlet. In some aspects, the coolant material is delivered to the coolant channels positioned within the plurality of catalyst support elements through the at least one coolant inlet.

In certain aspects, the reactor can further comprise a plurality of conduits wherein each conduit has a longitudinal axis that is parallel or substantially parallel to the longitudinal axis of the reactor. In yet other aspects, the at least one elongate catalyst support element can be positioned within each respective conduit. In still further aspects, each conduit of the plurality of conduits can be positioned in fluid communication with the at least one gas inlet.

In some aspects, the plurality of elongate catalyst support elements can be positioned in the reactor in any configuration chosen by one of ordinary skill in the art. For example, FIG. 4 shows an exemplary reactor having a plurality of elongate catalyst support elements 302 that are randomly dispersed within the reactor housing 300.

c. Exemplary Reactor Materials and Characteristics

It is understood that the reactors disclosed herein can have various cross-sectional shapes. As one of ordinary skill in the art would readily appreciate, the term "cross-section" as used herein refers to an intersection of a reactor body in three-dimensional space with a plane that is perpendicular to the longitudinal axis of the reactor. In some aspects, the reactor disclosed herein can have a rectangular or substantially rectangular cross-sectional shape. In yet other aspects, the reactor can have a rounded or substantially rounded cross-sectional shape. It is further understood that, for example, in the aspects wherein the frame is present, the housing and the frame can have complementary cross-sectional shapes that are optionally the same cross-sectional shape as the reactor. It is further understood that in some aspects, the reactor can have a cross-sectional shape that varies relative to the longitudinal axis of the reactor. For example, and without limitation, in some aspects, at least a first portion of the reactor can have a rounded or substantially rounded cross-sectional shape and at least a second portion of the reactor can have a rectangular or substantially rectangular cross-sectional shape. In other aspects, it is contemplated that at least a portion of an outer surface of the reactor can be tapered to produce a variable cross-sectional shape.

In some aspects, the longitudinal length of the reactor (relative to the longitudinal axis of the reactor) can range from about 0.5 m to about 20 m, including exemplary values of about 1 m, about 2 m, about 3 m, about 4 m, about 5 m, about 6 m, about 7 m, about 8 m, about 9 m, about 10 m, about 11 m, about 12 m, about 13 m, about 14 m, about 15 m, about 16 m, about 17 m, about 18 m, and about 19 m. Still further, the length of the reactor can be in any range derived from any two of the above stated values. For example, the length of the reactor can range from about 1 m to about 10 m, or from about 5 m to about 15 m, or from about 8 m to 18 m.

In some aspects, if a frame is positioned within the housing as disclosed herein, the frame can optionally have the same length as the reactor. In yet other aspects, the frame positioned within the housing can have a shorter length compared to the length of the reactor. In yet other aspects, the reactor can comprise two or more frames. In the aspects where two or more frames are present, the two or more frames can be positioned in a stacked configuration that is at least partially received within the housing. In yet further aspects, the stacked frames can be fully received within the housing. It is further understood that the length of the each frame can be easily determined by one of ordinary skill in the art depending on the specific application.

In other aspects, the cross-sectional dimensions of the reactor can be dependent on the cross-sectional shape of the reactor. In the aspects where the cross-sectional shape of the reactor is rectangular or substantially rectangular, the dimensions can be determined by a diagonal. In some aspects, the diagonal can range from about 0.1 m to about 5 m, including exemplary values of about 0.5 m, about 1 m, about 1.5 m, about 2 m, about 2.5 m, about 3 m, about 3.5 m, about 4 m, and about 4.5 m. Still further, the diagonal can be in any range derived from any two of the above stated values. For example, the diagonal can range from about 0.5 m to about 3 m, or from about 1 m to about 5 m.

In the aspects where the cross-sectional shape of the reactor is rounded or substantially rounded, the dimensions can be determined by a diameter. In some aspects, the diameter can range from about 0.1 m to about 5 m, including exemplary values of about 0.5 m, about 1 m, about 1.5 m, about 2 m, about 2.5 m, about 3 m, about 3.5 m, about 4 m, and about 4.5 m. Still further, the diameter can be in any range derived from any two of the above stated values. For example, the diameter can range from about 0.5 m to about 3 m, or from about 1 m to about 5 m.

In certain aspects, the housing of the reactor can be made from any materials known in the art and capable of withstanding processing conditions as disclosed herein. In some aspects, the housing of the reactor can be made from ceramic material, stainless steel, carbon steel, corrosion-resistant steel, copper, aluminum, aluminum alloy, or any combinations thereof. In certain aspects, the housing can be made of steel bound to metals selected from Groups 5-10 of the Periodic Table, for example and without limitation, vanadium, niobium, chromium, molybdenum, tungsten, manganese, nickel and the like. In yet other aspects, the ceramic material can comprise mullite ($Al_6Si_2O_{10}$), cordierite ($Mg_2Al_4Si_5O_{18}$), alumina, silica, silicon carbide, silicon nitride, alkaline earth oxides, spinel, magnesium aluminate spinel, titania, zirconia, transition metal oxides, or any combination thereof. In some other aspects, the housing can be made from zeolites.

In yet other aspects, the disclosed frame can be made from any materials known in the art and capable of withstanding processing conditions as disclosed herein. In some aspects, the frame can be made from ceramic material, stainless steel, carbon steel, corrosion-resistant steel, copper, aluminum, aluminum alloy, or any combinations thereof. In some aspects, the frame can be made of steel bound to metals selected from Groups 5-10 of the Periodic Table, for example and without limitation, vanadium, niobium, chromium, molybdenum, tungsten, manganese, nickel and the like. In yet other aspects, the ceramic material can comprise mullite ($Al_6Si_2O_{10}$), cordierite ($Mg_2Al_4Si_5O_{18}$), alumina, silica, silicon carbide, silicon nitride, alkaline earth oxides, spinel, magnesium aluminate spinel, titania, zirconia, transition metal oxides, or any combination thereof. In some other aspects, the frame can be made from zeolites.

In yet other aspects, the plurality of elongate catalyst support elements disclosed herein can be made from any materials known in the art and capable of withstanding processing conditions as disclosed herein. In some aspects, the elongate catalyst support elements can be made from ceramic material, stainless steel, carbon steel, corrosion-resistant steel, copper, aluminum, aluminum alloy, or any combinations thereof. In some aspects, the elongate catalyst support elements can be made of steel bound to metals selected from Groups 5-10 of the Periodic Table, for example and without limitation, vanadium, niobium, chromium, molybdenum, tungsten, manganese, nickel and the like. In yet other aspects, the ceramic material can comprise mullite ($Al_6Si_2O_{10}$), cordierite ($Mg_2Al_4Si_5O_{18}$), alumina, silica, silicon carbide, silicon nitride, alkaline earth oxides, spinel, magnesium aluminate spinel, titania, zirconia, transition metal oxides, or any combination thereof. In some other aspects, the plurality of elongate catalyst support elements can be made from zeolites.

It is further understood that in order to effectively transfer heat emitted or absorbed during the reactive processes carried out in each of the plurality of isolated conduits coated with the at least one catalyst material, the frame and/or the plurality of elongate catalyst support elements can be manufactured from a material exhibiting substantially high thermal conductivity, for example, material exhibiting an intrinsic thermal conductivity ranging from about 10 W/m/K to about 400 W/m/K, including exemplary values of about 20 W/m/K, about 50 W/m/K, about 100 W/m/K, about 150 W/m/K, about 200 W/m/K, about 250 W/m/K, about 300 W/m/K, and about 350 W/m/K. Still further, the intrinsic thermal conductivity of the material can be in any range derived from any two of the above stated values. For example, the intrinsic thermal conductivity of the material can range from about 10 W/m/K to about 100 W/m/K, or from about 50 W/m/K to about 200 W/m/K, or from about 100 W/m/K to about 350 W/m/K.

It is understood that the housing, the frame material, or material used for the plurality of elongate catalyst support elements can be selected by one of ordinary skill in the art depending on the processing conditions associated with a particular application.

In certain aspects, the plurality of conduits present in the disclosed reactors can have a rectangular or substantially rectangular cross-sectional shape. In other aspects, the plurality of conduits can have a square or substantially square cross-sectional shape. In other aspects, the plurality of conduits can have a rounded or substantially rounded cross-sectional shape. In yet other aspects, the plurality of conduits can have a triangular or substantially triangular cross-sectional shape. In certain aspects, each of the plurality of isolated conduits can have any dimensions determined by the one of ordinary skill in the art as beneficial to achieve desirable results. In some aspects, the dimensions of the each of the plurality of isolated conduits can be defined by a diagonal. In some aspects, the diagonal is from about 0.1 mm to about 50 mm, including exemplary values of about 0.2 mm, about 0.5 mm, about 1 mm, about 5 mm, about 10 mm, about 15 mm, about 20 mm, about 25 mm, about 30 mm, about 35 mm, about 40 mm, and about 45 mm. Still further, the diagonal can be in any range derived from any two of the above stated values. For example, the diagonal can be from about 0.5 mm to about 30 mm, or from about 1 mm to about 10 mm. In other aspects, the dimensions of the each of the plurality of isolated conduits can be defined by a diameter. In some aspects, the diameter is from about 0.1 mm to about 50 mm, including exemplary values of about 0.2 mm, about 0.5 mm, about 1 mm, about 5 mm, about 10 mm, about 15 mm, about 20 mm, about 25 mm, about 30 mm, about 35 mm, about 40 mm, and about 45 mm. Still further, the diameter can be in any range derived from any two of the above stated values. For example, the diameter can be from about 0.5 mm to about 30 mm, or from about 1 mm to about 10 mm.

In some aspects, the reactor has an open area corresponding to a void fraction ranging from about 40 to about 95%, including exemplary values of about 50%, about 60%, about 70%, about 80%, and about 90%.

In certain aspects, each conduit of the plurality of conduits as disclosed herein can be positioned in fluid communication with the at least one gas inlet. In some aspects, a feed gas entering the reactor from the at least one gas inlet can flow through the plurality of conduits. The desired exothermic or endothermic reaction can take place inside each of the plurality of conduits. For this purpose, in some aspects, the feed gas or a mixture of reactants can flow through the conduits where it is kept at the correct reaction temperature by means of thermal exchange with the coolant material circulating in the plurality of interconnected coolant channels as disclosed herein. In yet other aspects, the feed gas or a mixture of reactants can flow through the conduits where it is kept at the correct reaction temperature by means of thermal exchange with the coolant material circulating in the coolant channels defined by the plurality of elongate catalyst support elements as disclosed herein.

d. Exemplary Coolant Materials

In some aspects, the coolant materials disclosed herein can comprise any fluid known in the art that allows an effective heat transfer. In some aspects, the coolant material can include, for example and without limitation, any gas known in the art to conduct heat, molten salts, ionic liquids, water, steam, and the like. In some aspects, the at least one coolant material is selected from the group consisting of steam, water, molten salt, ionic liquid, flue gas and tube oil. In some aspects, the coolant material present in the plurality of interconnected coolant channels is not in direct contact with the at least one catalyst material coated on each conduit present in the frame. In yet other aspects, the coolant material present in the coolant channels within the plurality of catalyst support elements is not in contact with the at least one catalyst material present on the outer surface of each catalyst support element.

e. Exemplary Catalyst Materials

In some aspects, the at least one catalyst material can be disposed on the at least one exterior surface defining each conduit as disclosed herein. In yet other aspects, the at least one catalyst material can be disposed on the at least a portion of the outer surface of each catalyst support element as disclosed herein. In certain aspects, the at least one catalyst material can comprise washcoated monolithic catalyst (WMC) material.

In some aspects, the at least one catalyst material can comprise an inactive substrate with a relatively low specific surface area, and, lining the channels, a relatively high specific area catalyst substrate impregnated with a catalytically active material. In some aspects, the catalyst substrate and the active material can be deposited simultaneously on the at least one exterior surface that defines each conduit as disclosed herein. In other aspects, the catalyst substrate and the active material can be deposited simultaneously on each of the plurality of elongate catalyst support elements as disclosed herein. In certain aspects, the catalyst substrate is first deposited on the at least one exterior surface defining each conduit as disclosed herein and is subsequently impregnated with the active material. In yet other aspects, the catalyst substrate is first deposited on each of the plurality of elongate catalyst support elements as disclosed herein and then subsequently impregnated with the active material. In still other aspects, the at least one exterior surface that defines each conduit as disclosed herein can serve as a catalyst substrate. In yet other aspects, each of the plurality of elongate catalyst support elements as disclosed herein can serve as a catalyst substrate. It is further understood that impregnation of the catalyst substrate with the active catalyst material can be done by any methods known in the art. In yet other aspects, the at least one catalyst material can be deposited by any methods known in the art. In some aspects, the at least one catalyst material can be deposited in one step. In yet other aspects, the at least one catalyst material can be deposited in two or more steps.

In some aspects, the at least one catalyst material has an active and inactive phase. In certain aspects, the at least one catalyst material exhibits a uniform dispersion of active phase. In other aspects, the at least one catalyst material exhibits a uniform dispersion of active phase in axial and radial direction. In other aspects, the at least one catalyst material can have one or more activity zones. It is understood that a type of the activity zone and a number of the activity zones can be easily determined by one of ordinary skill in the art depending on a specific application.

In some aspects, the at least one catalyst material, for example, the Fisher-Tropsch catalyst can be prepared by impregnation of an active Fisher Tropsch metal or metal alloy and suitable promoters on a high-surface washcoated monolith or by washcoating the finished Fisher-Tropsch catalyst onto a low-surface monolith. In some aspects, the active Fisher-Tropsch metal or metal alloy can comprise Co, Fe, Ru, Ni, or any combinations thereof. In other aspects, the promoter can comprise Re, Pt, Ir, Rh, Pd, Ru, and any combinations thereof.

As one of ordinary skill in the art would readily appreciate, the arrangement of the at least one catalyst material will define an optimum compromise that can be obtained between the pressure drops of the feed flow along the reactor and the availability of suitable quantities of the at least one catalyst material per volume unit of the reactor. It is further understood that a composition of the at least one catalyst material is governed by kinetics, conversion and selective along with the heat transfer of the reactor. As one of ordinary skill in the art would readily appreciate, the composition of the at least one catalyst material will depend on the intrinsic kinetics of the reactions and transport phenomena.

In some aspects, the at least one catalyst material has a thickness ranging from about 10 µm to about 10,000 µm, including exemplary values of about 20 µm, about 30 µm, about 40 µm, about 50 µm, about 60 µm, about 70 µm, about 80 µm, about 100 µm, about 200 µm, about 300 µm, about 400 µm, about 500 µm, about 600 µm, about 700 µm, about 800 µm, about 900 µm, about 1,000 µm, about 2,000 µm, about 3,000 µm, about 4,000 µm, about 5,000 µm, about 6,000 µm, about 7,000 µm, about 8,000 µm, and about 9,000 µm. Still further, the thickness of the at least one catalyst material can be in any range derived from any two of the above stated values. For example, the thickness of the at least one catalyst material can range from about 40 µm to about 1,000 µm, or from about 100 µm to about 5,000 µm, or from about 500 µm to about 10,000 µm.

In some aspects, the at least one catalyst material has a uniform thickness regardless the cross-sectional shape of the plurality of conduits as disclosed herein. In certain aspects, where the conduits have a rectangular, substantially rectangular, square, substantially square, triangular, or substantially triangular cross-sectional shape, the thickness of the at least one catalyst material on the exterior surfaces of the conduits can vary about the outer circumference or perimeter of the conduit. In exemplary aspects, within conduits having polygonal cross-sectional shapes, the thickness of the at least one catalyst material can be greater at the corner portions defined by the conduits than along the edges connecting the corner portions.

In some aspects, the at least one catalyst material has a particle size ranging from about 0.5 nm to about 10 µm. In certain aspects, the particle size of the at least one catalyst material is selected so that it has a narrow distribution. In yet other aspects, the narrow distribution of the particle size results in a homogeneous catalyst material. In some aspects, the dimensions can be selected by one of ordinary skill in the art to allow an easy flow of the feed gas in the conduits and a uniform filling thereof, at the same time allowing the flow of the reaction mixture or the feed gas without high pressure drops.

f. Reactors Having Heat Transfer Assemblies

Further disclosed herein are reactors having a housing and at least one heat transfer assembly positioned within the housing. In some aspects, the housing has an outer wall, wherein the outer wall defines at least one gas inlet and at least one coolant inlet. In yet other aspects, each heat transfer assembly of the at least one heat transfer assembly comprises at least one coolant conduit. In yet further aspects, each heat transfer assembly of the at least one heat transfer assembly further comprises a plurality of flange elements. In some aspects, each coolant conduit of the at least one coolant conduit has an outer surface and a longitudinal axis that is parallel or substantially parallel to the longitudinal axis of the reactor. In certain aspects, each flange element of the plurality of flange elements is oriented perpendicularly or substantially perpendicularly relatively to the longitudinal axis of the reactor, wherein at least a portion of each flange element of the at least one heat transfer assembly is coated with at least one catalyst material. In yet other aspects, the at least one coolant conduit of the at least one heat transfer assembly is positioned in fluid communication with the at least one coolant inlet. In yet further aspects, each flange element of the at least one heat transfer assembly is positioned in fluid communication with the at least one gas inlet. In still further aspects, the at least one coolant conduit of the at least one heat transfer assembly is fluidly isolated from the at least one gas inlet.

In some aspects, each coolant conduit of the at least one heat transfer assembly has a rectangular or substantially rectangular cross-sectional shape. In other aspects, each coolant conduit of the at least one heat transfer assembly has a square or substantially square cross-sectional shape. In yet other aspects, each coolant conduit of the at least one heat transfer assembly has a rounded or substantially rounded cross-sectional shape.

In some aspects, each coolant conduit of the at least one heat transfer assembly can have any dimensions determined by one of ordinary skill in the art as beneficial to achieve desirable results. In some aspects, the dimensions of the each coolant conduit can be defined by a diagonal. In some aspects, the diagonal is from about 0.1 mm to about 50 mm, including exemplary values of about 0.2 mm, about 0.5 mm, about 1 mm, about 5 mm, about 10 mm, about 15 mm, about 20 mm, about 25 mm, about 30 mm, about 35 mm, about 40 mm, and about 45 mm. Still further, the diagonal can be in any range derived from any two of the above stated values. For example, the diagonal can be from about 0.5 mm to about 30 mm, or from about 1 mm to about 10 mm. In other aspects, the dimensions of each coolant conduit can be defined by a diameter. In some aspects, the diameter is from about 0.1 mm to about 50 mm, including exemplary values of about 0.2 mm, about 0.5 mm, about 1 mm, about 5 mm, about 10 mm, about 15 mm, about 20 mm, about 25 mm, about 30 mm, about 35 mm, about 40 mm, and about 45 mm. Still further, the diameter can be in any range derived from any two of the above stated values. For example, the diameter can be from about 0.5 mm to about 30 mm, or from about 1 mm to about 10 mm.

In some aspects, the at least one heat transfer assembly can comprise from about 1 to about 50,000 coolant conduits, including exemplary values of about 5, about 10, about 25, about 50, about 75, about 100, about 250, about 500, about 1,000, about 2,500, about 5,000, about 7,500, about 10,000, about 20,000, about 30,000, and about 40,000 coolant conduits. Still further, the at least one heat transfer assembly can comprise number of coolant conduits in any range derived from any two of the above stated values. For example, the at least one heat transfer assembly can comprise from about 1 to about 25 coolant conduits, about 10 to about 40,000 coolant conduits, or from about 100 to about 20,000 coolant conduits, or from about 1,000 to about 10,000 coolant conduits.

In yet other aspects, the heat transfer assembly can be made from any materials known in the art and capable of withstanding processing conditions as disclosed herein. In some aspects, the heat transfer assembly can be made from ceramic material, stainless steel, carbon steel, corrosion-resistant steel, copper, aluminum, aluminum alloy, or any combinations thereof. In some aspects, the heat transfer assembly can be made of steel bound to metals selected from Group 5-10 of Periodic Table, for example and without limitation, vanadium, niobium, chromium, molybdenum, tungsten, manganese, nickel and the like. In yet other aspects, the ceramic material can comprise mullite ($Al_6Si_2O_{10}$), cordierite ($Mg_2Al_4Si_5O_{18}$), alumina, silica, silicon carbide, silicon nitride, alkaline earth oxides, spinel, magnesium aluminate spinel, titania, zirconia, transition metal oxides, or any combination thereof. In some other aspects, the heat transfer assembly can be made from zeolites. In some aspects, each coolant conduit of the at least one coolant conduit and each flange element of the plurality of flange elements can be made from the same or different material, wherein the material can be selected by one of ordinary skill in the art depending on the processing conditions. It is further understood that material utilized in manufacturing the heat transfer assembly can be thermo-conductive and corrosion resistant.

It is further understood that in order to effectively transfer heat emitted or absorbed during the reactive processes carried out on at least a portion of each flange element of the at least one heat transfer assembly coated with at least one catalyst material, each flange element and each coolant conduit can be manufactured from the material exhibiting substantially high thermal conductivity, for example, material exhibiting an intrinsic thermal conductivity from about 10 W/m/K to about 400 W/m/K, including exemplary values of about 20 W/m/K, about 50 W/m/K, about 100 W/m/K, about 150 W/m/K, about 200 W/m/K, about 250 W/m/K, about 300 W/m/K, and about 350 W/m/K. Still further, the intrinsic thermal conductivity of the material can be in any range derived from any two of the above stated values. For example, the intrinsic thermal conductivity of the material can be from about 10 W/m/K to about 100 W/m/K, or from about 50 W/m/K to about 200 W/m/K, or from about 100 W/m/K to about 350 W/m/K.

In some aspects, the plurality of flange elements can comprise from about 2 to about 500 flange elements.

In certain aspects, the reactor has a rectangular or substantially rectangular cross-sectional shape. In some aspects, the reactor can have a square or substantially square cross-sectional shape. In yet other aspects, the reactor can have a rounded or substantially rounded cross-sectional shape. It is further understood that the reactor can have dimensions in any range disclosed herein. It is further understood that the reactor can be made of any materials disclosed herein. In some aspects, at least one heat transfer assembly comprises a plurality of heat transfer assemblies. In certain aspects, the plurality of heat transfer assemblies can comprise from about 2 to about 100 heat transfer assemblies.

Figure 5A:
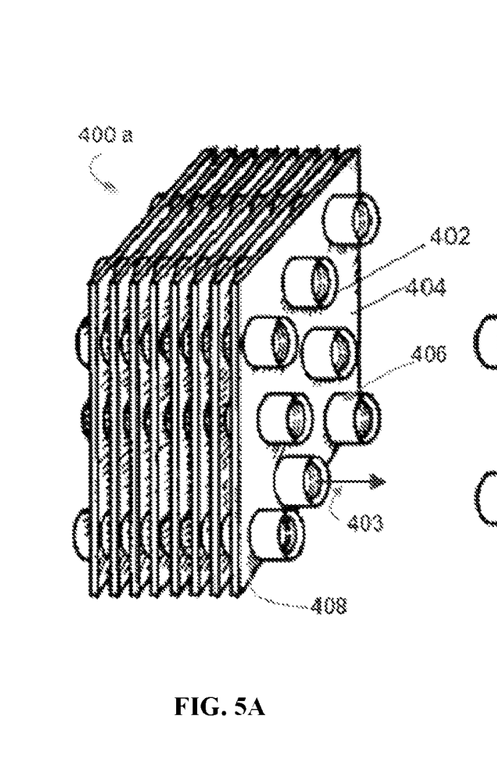
FIG. 5A is a perspective view of an exemplary heat transfer assembly as disclosed herein.

FIG. 5A demonstrates an exemplary heat transfer assembly 400a comprising a plurality of coolant conduits 402 and a plurality of flange elements 404. Each coolant conduit 402 can have a respective longitudinal axis 403 and an outer surface 406.

Figure 5B:
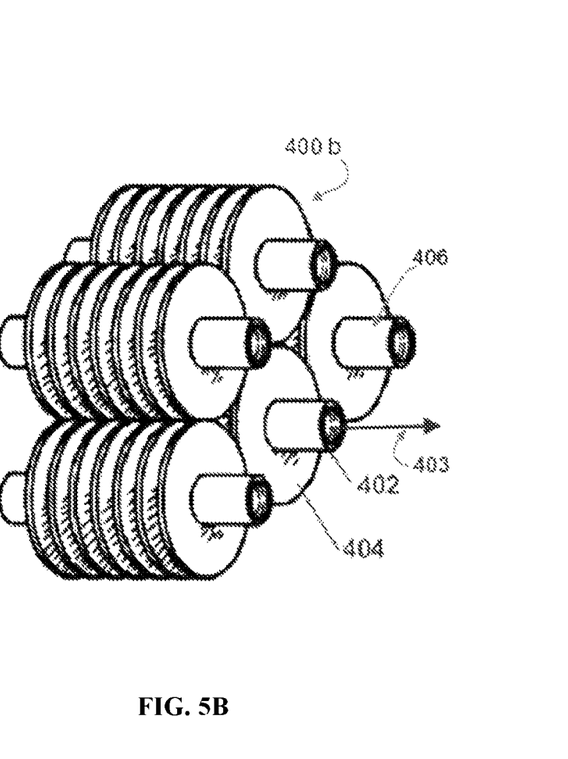
FIG. 5B is a perspective view of another exemplary heat transfer assembly as disclosed herein.

In certain aspects, and as depicted in FIG. 5B, the reactor described herein can comprise at least one heat transfer assembly 400b wherein each heat transfer assembly of the at least one heat transfer assembly comprises a single coolant conduit, the single coolant conduit having a length, wherein the plurality of flange elements are spaced along the length of the coolant conduit relative to the longitudinal axis of the coolant conduit. FIG. 5B demonstrates exemplary heat transfer assemblies 400b, wherein each heat transfer assembly comprises a single coolant conduit 402 and a plurality of flange elements 404.

In certain aspects, and with reference to FIG. 5A, each heat transfer assembly 400a can comprise a plurality of coolant conduits 402, wherein each flange element 404 of the plurality of flange elements of each heat transfer assembly defines a plurality of openings 408, and wherein each opening of the plurality of openings is configured to receive a respective coolant conduit of the plurality of coolant conduits. In some other aspects, the plurality of flange elements 404 of each heat transfer assembly 400a are spaced relative to the longitudinal axes 403 of the coolant conduits 402 of the heat assembly.

It is further understood that the plurality of coolant conduits can comprise one or more coolant materials. In some aspects, the plurality of coolant conduits are in fluid communication with at least one coolant inlet. In some aspects, the coolant material is delivered to the plurality of coolant conduits through the at least one coolant inlet.

In some aspects, the coolant material can comprise any fluid known in the art that allows an effective heat transfer. In some aspects, the coolant material can include, for example and without limitation, any gas known in the art to conduct heat, molten salts, ionic liquids, water, steam, and the like. In some aspects, the coolant material present in the plurality of coolant conduits is not in direct contact with the at least one catalyst material. In some aspects, the flow of coolant material in a first coolant conduit of the plurality of coolant conduits is in parallel to the flow of coolant material in a second coolant conduit of the plurality of coolant conduits. In yet other aspects, the flow of coolant material in a first coolant conduit of the plurality of coolant conduits is counter-flow to the flow of coolant material in a second coolant conduit of the plurality of coolant conduits. It is further understood that the flow rate of the coolant material in each coolant conduit can be adjustable depending on the specific application. It is further understood that the maximum and minimum flow rate of the coolant material in each coolant conduit depends on the dimensions of each coolant conduit and can be easily defined by one of ordinary skill in the art depending on the specific application.

It is further understood that any catalyst material disclosed herein can be utilized in the disclosed reactor. For example, it is contemplated that any catalyst material disclosed with respect to the reactors having interconnected coolant channels or elongate catalyst support elements can likewise be used with the reactors having heat transfer assemblies as disclosed herein.

3. Methods

Disclosed herein are methods of using the disclosed reactors in endothermic and/or exothermic catalytic processes. In some aspects, disclosed herein is a method of delivering at least one coolant material to the at least on coolant inlet of the reactor and delivering at least one gasification source material to the at least one gas inlet of the reactor.

In some aspects the gasification source material is selected from the group consisting of natural gas, biomass, and coal. In other aspects, the gasification source material is converted to a syngas. It is understood that the syngas can be generated from a variety of gasification materials that contain carbon. In some aspects, the syngas can be generated from biomass, plastics, coal, municipal waste, natural gas, or any combination thereof. In yet other aspects, the syngas can be generated from a fuel comprising methane. In some other aspects, the syngas generation from the fuel comprising methane can be based on steam reforming, autothermal reforming, a partial oxidation, or any combination thereof. In some aspects, the syngas is generated by a steam reforming. In these aspects, steam methane reforming uses an external source of hot gas to heat tubes in which a catalytic reaction takes place that converts steam and methane into a gas comprising hydrogen and carbon monoxide. In other aspects, the syngas is generated by autothermal reforming. In these aspects, methane is partially oxidized in a presence of oxygen and carbon dioxide or steam. In aspects, where oxygen and carbon dioxide are used to generate syngas from methane, the hydrogen and carbon monoxide can be produced in a ratio of about 1 to 1. In aspects, where oxygen and steam are utilized, the hydrogen and carbon monoxide can be produced in a ratio of about 2.5 to 1. In some aspects, the syngas is generated by a partial oxidation. In these aspects, a substoichiometric fuel-air mixture is partially combusted in a reformer, creating a hydrogen-rich syngas. In certain aspects, the partial oxidation can comprise a thermal partial oxidation and catalytic partial oxidation. In some aspects, the thermal partial oxidation is dependent on the air-fuel ration and proceed at temperatures of 1,200° C. or higher. In yet other aspects, in the catalytic partial oxidation, use of a catalyst can allow reduction of the required temperature to about 800° C. to 900° C. It is further understood that the choice of reforming technique can depend on the sulfur content of the fuel being used. The catalytic partial oxidation can be employed if the sulfur content is below 50 ppm. A higher sulfur content can poison the catalyst, and thus, other reforming techniques can be utilized.

In certain aspects, the generated syngas enters a reactor disclosed herein wherein the desired hydrocarbons are catalytically produced. In some aspects, the catalytic process comprises a Fisher-Tropsch reaction. The Fischer-Tropsch catalytic process for producing hydrocarbons from syngas is known in the art. Several reactions can take place in a Fischer-Tropsch process, such as, a Fischer-Tropsch (FT) reaction, a water gas shift reaction, and a hydrogen methanation, as shown in Scheme 1.

Scheme 1

FT reaction: $n\,CO + 2n\,H_2 \rightarrow (CH_2)_n + H_2O$

-continued

It is understood that the composition of syngas entering a Fischer-Tropsch reactor can vary significantly depending on the feedstock and the gasification process involved. In some aspects, the syngas composition can comprise from about 25 to about 60 wt. % carbon monoxide (CO), about 15 to about 50 wt. % hydrogen ($H_2$), from 0 to about 25 wt. % methane ($CH_4$), and from about 5 to about 45 wt. % carbon dioxide ($CO_2$). In yet other aspects, the syngas can further comprise nitrogen gas, water vapor, sulfur compounds such as for example, hydrogen sulfide ($H_2S$) and carbonyl sulfide (COS). In yet other aspects, the syngas can further comprise ammonia and other trace contaminants.

The main gases that are being mixed in the Fischer-Tropsch process described herein comprise $H_2$ and CO. In some aspects, the $H_2$/CO molar ratio of the feed can be from about 0.5 to about 4. In some exemplary aspects, the $H_2$/CO molar ratio can be from about 1.0 to about 3.0. In other exemplary aspects, the $H_2$/CO molar ratio can be from about 1.5 to about 3.0, or yet further exemplary aspects, the $H_2$/CO molar ratio can be from about 1.5 to about 2.5. It will be appreciated that the $H_2$/CO molar ratio can control the selectivity of the hydrocarbons that are being produced. The consumption molar ratio of $H_2$/CO is usually from about 1.0 to about 2.5, such as for example, from about 1.5 to 2.1. This ratio increases as long as the water gas shift reaction is active, and thus, the use of a feed ratio below the consumption ratio will result in a stable $H_2$/CO ratio during the reaction within an acceptable range (normally below about 2). The $H_2$ and CO are catalytically reacted in a Fischer-Tropsch reaction.

In some aspects, the chemical reaction, for example, a Fischer-Tropsch reaction, produces gaseous hydrocarbons selected from the group consisting of a lower olefin, a lower paraffin, and a lower alcohol. In some aspects, the lower olefin, a lower paraffin and a lower alcohol comprise olefins, paraffins and alcohols having C2-C6 hydrocarbons. In other aspects, the chemical reaction produces liquid hydrocarbons selected from the group consisting of a higher olefin, a higher paraffin, and a higher alcohol. In some aspects, the higher olefin, a higher paraffin and a higher alcohol comprise olefins, paraffins and alcohols having C7-C20 hydrocarbons.

In further aspects, the at least one coolant material is selected from the group consisting of steam, water, molten salt, ionic liquid, flue gas, and lube oil.

It is understood that the reactors and methods described herein provide an effective control over endothermic and exothermic catalytic reactions, such as Fisher-Tropsch reactions.

4. Aspects

In view of the described reactors and methods and variations thereof, herein below are described certain more particularly described aspects of the invention. These particularly recited aspects should not however be interpreted to have any limiting effect on any different claims containing different or more general teachings described herein, or that the "particular" aspects are somehow limited in some way other than the inherent meanings of the language and formulas literally used therein.

Aspect 1: A reactor having a longitudinal axis, the reactor comprising: a housing having an outer wall, the outer wall defining at least one gas inlet and at least one coolant inlet; a frame positioned within the housing, the frame comprising a plurality of interior surfaces and a plurality of exterior surfaces, wherein the plurality of interior surfaces cooperate to define a plurality of interconnected coolant channels within the frame, wherein the plurality of exterior surfaces define a plurality of isolated conduits, each conduit of the plurality of isolated conduits having a respective longitudinal axis that is parallel or substantially parallel to the longitudinal axis of the reactor, wherein at least a portion of the at least one exterior surface that defines each respective conduit is coated with at least one catalyst material to position the at least one catalyst material within the conduit, wherein the plurality of interconnected coolant channels are positioned in fluid communication with the at least one coolant inlet, and wherein the plurality of conduits are positioned in fluid communication with the at least one gas inlet.

Aspect 2: The reactor of aspect 1, wherein the plurality of interconnected coolant channels of the frame comprise a first plurality of coolant channels and a second plurality of coolant channels, wherein the second plurality of coolant channels are oriented perpendicularly or substantially perpendicularly to the first plurality of coolant channels to thereby create a grid of coolant channels.

Aspect 3: The reactor of aspect 1 or aspect 2, wherein the plurality of conduits have a rectangular or substantially rectangular cross-sectional shape.

Aspect 4: The reactor of aspect 1 or aspect 2, wherein the plurality of conduits have a square or substantially square cross-sectional shape.

Aspect 5: The reactor of aspect 1 or aspect 2, wherein the plurality of conduits have a rounded cross-sectional shape.

Aspect 6: The reactor of any one of aspects 2-5, wherein the first plurality of coolant channels have longitudinal axes that extend perpendicularly or substantially perpendicularly to the longitudinal axes of the plurality of conduits, and wherein each coolant channel of the second plurality of coolant channels has a variable profile that extends and is angled relative to the longitudinal axes of the first plurality of coolant channels.

Aspect 7: The reactor of aspect 6, wherein the variable profile of each coolant channel of the second plurality of coolant channels corresponds to a serpentine or substantially serpentine pattern extending between and in fluid communication with adjacent coolant channels of the first plurality of coolant channels.

Aspect 8: The reactor of any one of the preceding aspects, wherein the plurality of conduits have a triangular or substantially triangular cross-sectional shape.

Aspect 9: The reactor of any one of the preceding aspects, wherein the reactor has a rectangular or substantially rectangular cross-sectional shape.

Aspect 10: The reactor of any one of aspects 1-8, wherein the reactor has a rounded or substantially rounded cross-sectional shape.

Aspect 11: The reactor of any one of aspects 1-10, wherein the at least one catalyst material has a thickness ranging from about 10 μm to about 10,000 μm.

Aspect 12: The reactor of aspect 11, wherein the at least one catalyst material has a thickness ranging from about 40 μm to about 1,000 μm.

Aspect 13: A method using the reactor of any one of the preceding aspects, comprising: delivering at least one coolant material to the at least one coolant inlet of the reactor; and delivering at least one gasification source material to the at least one gas inlet of the reactor.

Aspect 14: The method of aspect 13, wherein the gasification source material is selected from the group consisting of natural gas, biomass, and coal.

Aspect 15: The method of aspect 13 or aspect 14, wherein the chemical reaction produces gaseous hydrocarbons selected from the group consisting of a lower olefin, a lower paraffin, and a lower alcohol.

Aspect 16: The method of any one of aspects 13-15, wherein the chemical reaction produces liquid hydrocarbons selected from the group consisting of a higher olefin, a higher paraffin, and a higher alcohol.

Aspect 17: The method of any one of aspects 13-16, wherein the chemical reaction is a Fischer Tropsch reaction.

Aspect 18: The method of any one of aspects 13-17, wherein the at least one coolant material is selected from the group consisting of steam, water, molten salt, ionic liquid, flue gas, and lube oil.

Aspect 19: A reactor having a longitudinal axis, the reactor comprising: a housing having an outer wall, the outer wall defining at least one gas inlet and at least one coolant inlet; and a plurality of elongate catalyst support elements, each catalyst support element having an inner surface and an outer surface, the inner surface of each catalyst support element defining a coolant channel within the catalyst support element, wherein at least a portion of the outer surface of each catalyst support element is coated with at least one catalyst material, wherein the coolant channels of the plurality of catalyst support elements are positioned in fluid communication with the at least one coolant inlet, wherein the outer surfaces of the plurality of catalyst support elements are positioned in fluid communication with the at least one gas inlet, and wherein the coolant channels of the plurality of elongate catalyst support elements are fluidly isolated from the at least one gas inlet.

Aspect 20: The reactor of aspect 19, wherein the at least one elongate catalyst support element comprises a flexible material.

Aspect 21: The reactor of aspect 19 or aspect 20, wherein the plurality of elongate catalyst support elements are randomly dispersed within the housing.

Aspect 22: The reactor of any one of aspects 19-21, wherein the reactor has a rectangular or substantially rectangular cross-sectional shape.

Aspect 23: The reactor of any one of aspects 19-21, wherein the reactor has a rounded or substantially rounded cross-sectional shape.

Aspect 24: The reactor of any one of aspects 19-23, further comprising a plurality of conduits, each conduit having a longitudinal axis that is parallel or substantially parallel to the longitudinal axis of the reactor, wherein at least one elongate catalyst support element is positioned within each respective conduit, and wherein each conduit of the plurality of conduits is positioned in fluid communication with the at least one gas inlet.

Aspect 25: The reactor of aspect 24, wherein each conduit of the plurality of conduits has a rectangular or substantially rectangular cross-sectional shape.

Aspect 26: The reactor of aspect 24, wherein each conduit of the plurality of conduits has a square or substantially square cross-sectional shape.

Aspect 27: The reactor of aspect 24, wherein each conduit of the plurality of conduits has a rounded cross-sectional shape.

Aspect 28: A method using the reactor of any one of aspects 19-27, comprising: delivering at least one coolant material to the at least one coolant inlet of the reactor; and delivering at least one gasification source material to the at least one gas inlet of the reactor.

Aspect 29: The method of aspect 28, wherein the gasification source material is selected from the group consisting of natural gas, biomass, and coal.

Aspect 30: The method of aspect 28 or aspect 29, wherein the chemical reaction produces gaseous hydrocarbons selected from the group consisting of a lower olefin, a lower paraffin, and a lower alcohol.

Aspect 31: The method of any one of aspects 28-30, wherein the chemical reaction produces liquid hydrocarbons selected from the group consisting of a higher olefin, a higher paraffin, and a higher alcohol.

Aspect 32: The method of any one of aspects 28-31, wherein the chemical reaction is a Fischer Tropsch reaction.

Aspect 33: The method of any one of aspects 28-32, wherein the at least one coolant material is selected from the group consisting of steam, water, molten salt, ionic liquid, flue gas, and lube oil.

Aspect 34: A reactor having a longitudinal axis, the reactor comprising: a housing having an outer wall, the outer wall defining at least one gas inlet and at least one coolant inlet; and at least one heat transfer assembly positioned within the housing, at least one heat transfer assembly positioned within the housing, each heat transfer assembly of the at least one heat transfer assembly comprising at least one coolant conduit and a plurality of flange elements, each coolant conduit of the at least one coolant conduit having an outer surface and a longitudinal axis that is parallel or substantially parallel to the longitudinal axis of the reactor, each flange element of the plurality of flange elements is oriented perpendicularly or substantially perpendicularly relatively to the longitudinal axis of the reactor, wherein at least a portion of each flange element of the at least one heat transfer assembly is coated with at least one catalyst material, wherein at least a portion of each flange element of the at least one heat transfer assembly is coated with at least one catalyst material, wherein the at least one coolant conduit of the at least one heat transfer assembly is positioned in fluid communication with the at least one coolant inlet, wherein each flange element of the at least one heat transfer assembly is positioned in fluid communication with the at least one gas inlet, and wherein the at least one coolant conduit of the at least one heat transfer assembly is fluidly isolated from the at least one gas inlet.

Aspect 35: The reactor of aspect 34, wherein each coolant conduit of the at least one heat transfer assembly has a rectangular or substantially rectangular cross-sectional shape.

Aspect 36: The reactor of aspect 34, wherein each coolant conduit of the at least one heat transfer assembly has a square or substantially square cross-sectional shape.

Aspect 37: The reactor of aspect 34, wherein each coolant conduit of the at least one heat transfer assembly has a rounded or substantially rounded cross-sectional shape.

Aspect 38: The reactor of any one of aspects 34-37, wherein the reactor has a rectangular or substantially rectangular cross-sectional shape.

Aspect 39: The reactor of any one of aspects 34-37, wherein the reactor has a square or substantially square cross-sectional shape.

Aspect 40: The reactor of any one of aspects 34-37, wherein the reactor has a rounded or substantially rounded cross-sectional shape.

Aspect 41: The reactor of any one of aspects 34-40, wherein each heat transfer assembly comprises a single coolant conduit, the single coolant conduit having a length, wherein the plurality of flange elements are spaced along the length of the coolant conduit relative to the longitudinal axis of the coolant conduit.

Aspect 42: The reactor of any one of aspects 34-40, wherein each heat transfer assembly comprises a plurality of coolant conduits, wherein each flange element of the plurality of flange elements of each heat transfer assembly each heat transfer assembly comprises a plurality of coolant conduits, wherein each flange element of the plurality of flange elements of each heat transfer assembly defines a plurality of openings, wherein each opening of the plurality of openings of each heat transfer assembly is configured to receive a respective coolant conduit of the plurality of coolant conduits.

Aspect 43: The reactor of aspect 42, wherein the plurality of flange elements of each heat transfer assembly are spaced relative to the longitudinal axes of the coolant conduits of the heat assembly.

Aspect 44: The reactor of any one of aspects 34-43, wherein the at least one heat transfer assembly comprises a plurality of heat transfer assemblies.

Aspect 45: A method using the reactor of any one of aspects 34-44, comprising: delivering at least one coolant material to the at least one coolant inlet of the reactor; and delivering at least one gasification source material to the at least one gas inlet of the reactor.

Aspect 46: The method of aspect 45, wherein the gasification source material is selected from the group consisting of natural gas, biomass, and coal.

Aspect 47: The method of aspect 45 or aspect 46, wherein the chemical reaction produces gaseous hydrocarbons selected from the group consisting of a lower olefin, a lower paraffin, and a lower alcohol.

Aspect 48: The method of any one of aspects 45-47, wherein the chemical reaction produces liquid hydrocarbons selected from the group consisting of a higher olefin, a higher paraffin, and a higher alcohol.

Aspect 49: The method of any one of aspects 45-48, wherein the chemical reaction is a Fischer Tropsch reaction.

Aspect 50: The method of any one of aspects 45-49, wherein the at least one coolant material is selected from the group consisting of steam, water, molten salt, ionic liquid, flue gas, and lube oil.

What is claimed is:

1. A reactor having a longitudinal axis, the reactor comprising:
    a housing having an outer wall, the outer wall defining at least one gas inlet and at least one coolant inlet;
    a frame positioned within the housing, the frame having a longitudinal length and comprising a plurality of interior surfaces and a plurality of exterior surfaces, wherein the plurality of interior surfaces cooperate to define a plurality of interconnected coolant channels within the frame, wherein the plurality of exterior surfaces define a plurality of isolated conduits, each conduit of the plurality of isolated conduits having a respective longitudinal axis that is substantially parallel to the longitudinal axis of the reactor, wherein at least a portion of the at least one exterior surface that defines each respective conduit is coated with at least one catalyst material to position the at least one catalyst material within the conduit,
    wherein the plurality of interconnected coolant channels are positioned in fluid communication with the at least one coolant inlet,
    wherein the plurality of conduits are positioned in fluid communication with the at least one gas inlet,
    wherein within a cross-sectional plane that is perpendicular to the longitudinal axis of the reactor, each coolant channel of the plurality of interconnected coolant channels is fluidly connected with each of the other coolant channels of the plurality of coolant channels,
    wherein, within the cross-sectional plane, each respective isolated conduit of the plurality of isolated conduits is defined between intersecting and fluidly connected portions of at least two coolant channels of the plurality of interconnected coolant channels,
    wherein, within the cross-sectional plane, at least one isolated conduit of the plurality of isolated conduits is cooperatively defined by the outer wall of the housing and exterior surfaces of the frame, and
    wherein the plurality of isolated conduits and the plurality of interconnected coolant channels extend the length of the frame.

2. The reactor of claim 1, wherein the plurality of interconnected coolant channels of the frame comprise a first plurality of coolant channels and a second plurality of coolant channels, wherein within the cross-sectional plane, the second plurality of coolant channels are oriented substantially perpendicularly to the first plurality of coolant channels to thereby create a grid of coolant channels.

3. The reactor of claim 1, wherein the plurality of conduits have a substantially rectangular cross-sectional shape.

4. The reactor of claim 1, wherein the plurality of conduits have a substantially square cross-sectional shape.

5. The reactor of claim 1, wherein the plurality of conduits have a rounded cross-sectional shape.

6. The reactor of claim 1, wherein the plurality of interconnected coolant channels of the frame comprise a first plurality of coolant channels and a second plurality of coolant channels, wherein within the cross-sectional plane:
    the first plurality of coolant channels have longitudinal axes that extend substantially perpendicularly to the longitudinal axes of the plurality of conduits; and
    each coolant channel of the second plurality of coolant channels has a variable profile that extends and is angled relative to the longitudinal axes of the first plurality of coolant channels.

7. The reactor of claim 6, wherein the variable profile of each coolant channel of the second plurality of coolant channels corresponds to a substantially serpentine pattern extending between and in fluid communication with adjacent coolant channels of the first plurality of coolant channels.

8. The reactor of claim 1, wherein the reactor has a substantially rectangular cross-sectional shape.

9. The reactor of claim 1, wherein the reactor has a substantially rounded cross-sectional shape.

10. The reactor of claim 1, wherein the at least one catalyst material has a thickness ranging from about 10 µm to about 10,000 µm.

11. The reactor of claim 10, wherein the at least one catalyst material has a thickness ranging from about 40 µm to about 1,000 µm.

12. The reactor of claim 2, wherein the frame has a diameter, wherein within the cross-sectional plane, each coolant channel of the first plurality of coolant channels extends continuously across the diameter of the frame.

13. The reactor of claim 12, wherein within the cross-sectional plane, each coolant channel of the first plurality of coolant channels has a respective longitudinal axis extending continuously across the diameter of the frame.

14. The reactor of claim 1, wherein the at least one gas inlet comprises a first gas inlet, wherein the at least one coolant inlet comprises a first coolant inlet, wherein the first gas inlet and the first coolant inlet are positioned at opposing ends of the housing relative to the longitudinal axis, and wherein the plurality of isolated conduits and the plurality of interconnected coolant channels extend a length of the housing between the first gas inlet and the first coolant inlet.

15. A method comprising:
    delivering at least one coolant material to at least one coolant inlet of a reactor, the reactor having a longitudinal axis and comprising:
        a housing having an outer wall, the outer wall defining at least one gas inlet and the at least one coolant inlet;
        a frame positioned within the housing, the frame having a longitudinal length and comprising a plurality of interior surfaces and a plurality of exterior surfaces, wherein the plurality of interior surfaces cooperate to define a plurality of interconnected coolant channels within the frame, wherein the plurality of exterior surfaces define a plurality of isolated conduits, each conduit of the plurality of isolated conduits having a respective longitudinal axis that is substantially parallel to the longitudinal axis of the reactor, wherein at least a portion of the at least one exterior surface that defines each respective conduit is coated with at least one catalyst material to position the at least one catalyst material within the conduit,
    wherein the plurality of interconnected coolant channels are positioned in fluid communication with the at least one coolant inlet,
    wherein the plurality of conduits are positioned in fluid communication with the at least one gas inlet,
    wherein within a cross-sectional plane that is perpendicular to the longitudinal axis of the reactor, each coolant channel of the plurality of interconnected coolant channels is fluidly connected with each of the other coolant channels of the plurality of coolant channels,
    wherein, within the cross-sectional plane, each respective isolated conduit of the plurality of isolated conduits is defined between intersecting and fluidly connected portions of at least two coolant channels of the plurality of interconnected coolant channels,
    wherein, within the cross-sectional plane, at least one isolated conduit of the plurality of isolated conduits is cooperatively defined by the outer wall of the housing and exterior surfaces of the frame, and
    wherein the plurality of isolated conduits and the plurality of interconnected coolant channels extend the length of the frame; and
    delivering at least one gasification source material to the at least one gas inlet of the reactor.

16. The method of claim 15, wherein the gasification source material is selected from the group consisting of natural gas, biomass, and coal.

17. The method of claim 15, wherein the chemical reaction produces gaseous hydrocarbons selected from the group consisting of a lower olefin, a lower paraffin, and a lower alcohol.

18. The method of claim 15, wherein the chemical reaction produces liquid hydrocarbons selected from the group consisting of a higher olefin, a higher paraffin, and a higher alcohol.

19. The method of claim 15, wherein the chemical reaction is a Fischer Tropsch reaction.

20. The method of claim 15, wherein the at least one coolant material is selected from the group consisting of steam, water, molten salt, ionic liquid, flue gas, and lube oil.

* * * * *